United States Patent [19]
Szajewski et al.

[11] Patent Number: 5,221,600
[45] Date of Patent: Jun. 22, 1993

[54] PHOTOGRAPHIC ELEMENTS CONTAINING DEVELOPMENT ACCELERATOR RELEASE COMPOUNDS

[75] Inventors: Richard P. Szajewski; Jerrold N. Poslusny, both of Rochester, N.Y.

[73] Assignee: Eastman Kodak Company, Rochester, N.Y.

[21] Appl. No.: 626,811

[22] Filed: Dec. 13, 1990

[51] Int. Cl.$^5$ ................................. G03C 1/02
[52] U.S. Cl. .................... 430/566; 430/543; 430/955; 430/958; 430/959
[58] Field of Search ............... 430/543, 558, 566, 955, 430/959, 958

[56] References Cited

U.S. PATENT DOCUMENTS

| | | | |
|---|---|---|---|
| 4,482,629 | 11/1984 | Nakagawa et al. | 430/542 |
| 4,618,572 | 10/1986 | Mihayashi et al. | 430/543 |
| 4,656,123 | 4/1987 | Mihayashi et al. | 430/543 |
| 4,724,197 | 2/1988 | Matejec et al. | 430/546 |
| 4,734,357 | 3/1988 | Mihayashi et al. | 430/553 |
| 4,820,616 | 4/1989 | Matejec et al. | 430/543 |
| 5,135,839 | 8/1992 | Szajewski | 430/544 |

Primary Examiner—Hoa Van Le
Attorney, Agent, or Firm—Joshua G. Levitt

[57] ABSTRACT

Certain development inhibitor releasing compounds when incorporated in a photographic element at low levels provide development acceleration. The compounds release silver halide binding groups that are substituted with a group containing an ether oxygen atom and/or an imino nitrogen atom. They are especially useful in high speed color photographic materials.

9 Claims, No Drawings

PHOTOGRAPHIC ELEMENTS CONTAINING DEVELOPMENT ACCELERATOR RELEASE COMPOUNDS

This invention relates to color photographic materials. In particular, it relates to such materials that contain a development accelerator releasing compound.

BACKGROUND OF THE INVENTION

Color photographic images are commonly formed by reaction between oxidized silver halide developing agent and a dye forming compound called a coupler. There are commonly included in the element various compounds that modify the image forming reaction and thereby modify the resulting color image.

It is known to incorporate compounds which release a development accelerator during development. Such compounds are described in, for example, U.S. Pat. No. 4,390,618; EP Published Patent Applications 117,511 and 118,087; and German Published Patent Applications 3,333,355; 3,410,616; and 3,428,545. These compounds release in an imagewise manner during development a development accelerator comprising a silver halide reducing moiety such as a hydrazide, a thiourea, a thiohydantoin or a rhodanine.

It is also known to incorporate in color photographic materials development inhibitor releasing (DIR) compounds which release a development inhibitor in an imagewise fashion during development. Such compounds are described in, for example, U.S. Pat. Nos. 3,227,554; 4,782,012; and in *Research Disclosure*, December 1989, Item 308119, Section VIIF, published by Kenneth Mason Publications Lts., The Old Harbourmasters, 8 North Street, Emsworth, Hampshire P010 7DD England. They release a silver halide binding group, such as a mercapto tetrazole or a benzotriazole.

A problem with using two different types of compounds for these two different purposes is that it is necessary to maintain supplies of two different materials. Another problem with using development accelerators that are electroactive, as are most of the groups described as development accelerators for release during photographic processing, is that they are susceptible to oxidative degradation during storage.

Thus, it would be desirable to be able to use one type of compound for both functions.

SUMMARY OF THE INVENTION

We have found that when certain compounds previously known only as development inhibitor releasing compounds are incorporated in photographic elements at low levels, they act as development accelerators. The moieties that behave in this way comprise a silver halide binding group to which is joined a substituent (Q) that contains an ether oxygen atom and/or an imino nitrogen atom, the substituent being free of silver halide bonding sites.

The effect of the compound as a development inhibitor or development accelerator is identified by measurement of the contrast (gamma, $\gamma$) of the processed film. Gamma is defined as the change in density produced after development as a function of the change in exposure expressed on log terms. See the *SPSE Handbook of Photographic Science and Engineering*, W. Thomas Jr. ed., Page 817, John Wiley and Sons, New York, 1973. In comparison with a material which differs only by the omission of the compound being tested, an increase in gamma indicates that the compound being tested, is acting as a development accelerator while a decrease in gamma indicates that the compound is acting as a development inhibitor.

The behavior of the compounds of this invention as development accelerators when incorporated in photographic elements at low levels is unexpected since U.S. Pat. No. 4,315,070 indicates that when DIR compounds are incorporated in color photographic materials at low levels, they have the effect of reducing fog formation.

Thus, in accordance with this invention there is provided a photographic element having a support and a development accelerator releasing (DAR) compound that releases a silver halide binding moiety having a substituent (Q) that contains an ether oxygen and/or an imino nitrogen group, the compound being present in the element in an amount such that when processed, the element provides an increase in contrast ($\gamma$) compared to an element identically formulated and processed except that it does not contain the development accelerator releasing compound.

In a preferred embodiment of this invention the DAR compound releases a development accelerator having the structure:

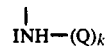

where
- INH is a silver halide binding group,
- Q is an aliphatic or alicyclic group of 2 to 30 carbon atoms which comprises an ether oxygen and/or imino nitrogen and is free of silver halide bonding sites, and
- k is 1–4.

In a more preferred embodiment of this invention the DAR compound releases a development accelerator having the structure

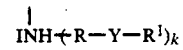

where
- INH and k are as defined above,
- R is an optionally substituted alkylene or cycloalkylene of 2–10 carbon atoms;
- Y is

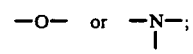

- $R^1$ is an optionally substituted alkyl or cycloalkyl of 1 to 6 carbon atoms when Y is —O—, or
- $R^1$ is an optionally substituted alkylene or cycloalkylene of 1 to 6 carbon atoms when Y is

the unsatisfied bond of N being joined to $R^1$; and R and $R^1$ may be joined to form a cyclic structure.

The alkylene or cycloalkylene groups completed by R include ethylene, propylene, isopropylene, butylene, isobutylene, t-butylene, pentylene, hexylene, octylene, nonylene, decylene, cyclopropylene, cyclobutylene, cyclopentylene, cyclohexylene, bicyclo-octylene, bicyclo-decylene and such groups further substituted with alkyl groups such as methyl, ethyl, propyl, butyl, and heteroatom groups such as hydroxy, alkoxy, amino, alkylamino, carbonyl, oxo, sulfoxide, sulfone, sulfo, sulfonyl, nitro, fluoro, chloro, bromo, iodo, etc.

When Y is

and R¹ is joined to N as indicated, then R¹ is like R.

When Y is —O— then R¹ is alkyl such as methyl, ethyl, propyl, isopropyl, cyclopropyl, butyl, isobutyl, sec-butyl, tert-butyl, cyclobutyl, pentyl, cyclopentyl, tert-pentyl, hexyl, cyclohexyl and so forth. The R¹ group can be substituted with the same substituents as identified above for R.

Carbon atoms in R and R¹ can be replaced by —O— or

groups to form additional ether oxygen and/or imino-nitrogen groups.

The substituents in R and R¹ are both free of silver halide bonding sites.

The development accelerator moiety

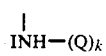

as defined above comprises between one and six ether oxygen and/or imino-nitrogen groups.

Especially preferred are development accelerators releasing coupled with release moieties which have one of the structures:

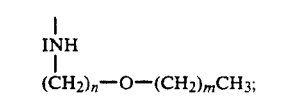

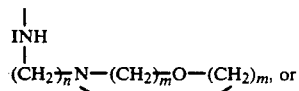

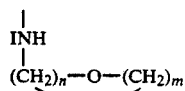

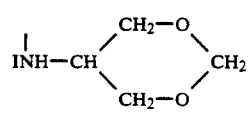

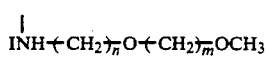

where each n is independently an integer of 2 to 5 and m is an integer of 2 to 6.

As used herein, the term "ether oxygen" refers to a bivalent oxygen atom wherein each of the two valencies is satisfied by a distinct carbon atom even though the carbon atom is further substituted, e.g. with an oxo group. As used herein, the term "imino nitrogen" refers to a tervalent nitrogen atom wherein each of the three valencies is satisfied by a distinct carbon atom. These ether oxygen and imino nitrogen atoms are referred to as "accelerator groups."

As used herein silver halide binding groups have sulfur, selenium, tellurium or heterocyclic nitrogen or carbon with a free valence that can form a bond to a silver atom.

Substituent silver halide bonding sites includes C=C and C=N groups as described in U.S. Pat. No. 4,962,018 and thioether groups (—S—) as described in U.S. patent application Ser. No. 366,730 filed Jun. 15, 1989.

As the number of ether oxygen and/or imino nitrogen atoms is increased, the accelerating function is likewise increased.

In a particularly preferred embodiment of this invention a Q group of the DAR compound as defined above comprises more than one ether oxygen and/or imino-nitrogen groups.

Examples of useful silver halide binding groups represented by the INH part of INH-Q are: oxazoles, thiazoles, diazoles, triazoles, oxadiazoles, thiadiazoles, oxathiazoles, thiatriazoles, benzotriazoles, tetrazoles, benzimidazoles, indazoles, isoindazoles, mercaptotetrazoles, selenotetrazoles, mercaptobenzothiazoles, selenobenzothiazoles, mercaptobenzoxazoles, selenobenzoxazoles, mercaptobenzimidazoles, selenobenzimidazoles, benzodiazoles, mercaptooxazoles, mercaptothiadiazoles, mercaptothiazoles, mercaptotriazoles, mercaptooxadiazoles, mercaptodiazoles, mercaptooxathiazoles, telleurotetrazoles or benzisodiazoles. Preferred development inhibitor groups (INH) are heterocyclic groups derived from tetrazoles, mercaptotetrazoles and benzotriazoles.

Typical examples of useful silver halide binding groups (INH) are as follows.

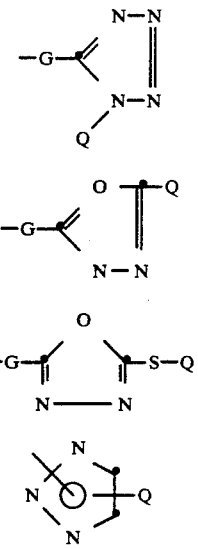

-continued

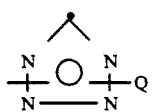
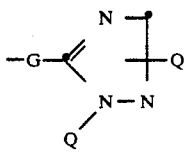
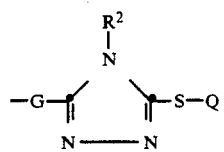
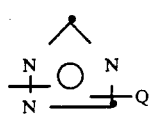
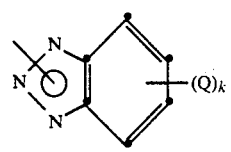
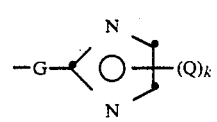
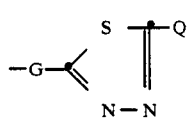
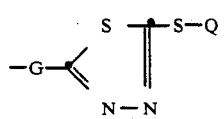
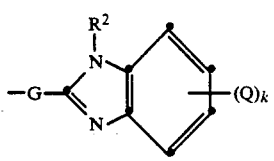
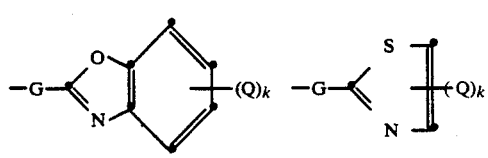
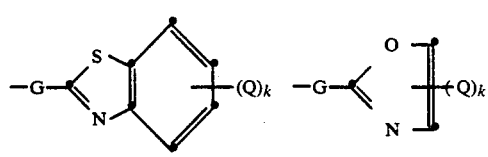

-continued

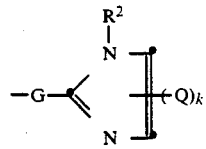
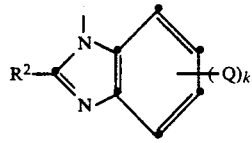
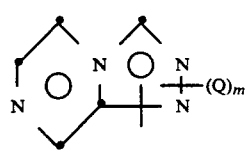
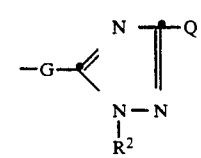
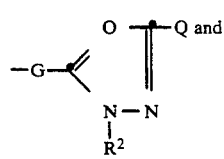 and
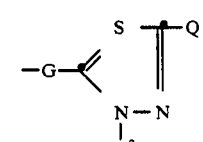

wherein G is S, Se or Te and $R^2$ is hydrogen or an unsubstituted or substituted hydrocarbon group, such as methyl, ethyl, propyl, n-butyl, phenyl, or is Q.

The silver halide binding moiety can be substituted with other groups that do not adversely affect the desired properties of INH.

The Q moiety may be unchanged as the result of exposure to photographic processing solution. However, Q may change in structure and effect as the result of photographic processing as disclosed in U.K. Patent No. 2,099,167, European patent application 167,168, Japanese Kokai 205150/83 or U.S. Pat. No. 4,782,012.

The development accelerator can be attached to any moiety from which it can be released during the development step. Typically, the compound contains a carrier group from which the accelerator is released either directly or from an intervening timing group which is first released from the carrier group.

Carrier groups useful in DAR-compounds of this invention include various known groups from which the development accelerator can be released by a variety of mechanisms. Representative carrier groups are described, for example, in U.S. Pat. No. 3,227,550 and Canadian Patent No. 602,607 (release by chromogenic coupling); U.S. Pat. Nos. 3,443,939 and 3,443,940 (release by intramolecular ring closure); U.S. Pat. Nos. 3,628,952, 3,698,987, 3,725,062, 3,728,113, 3,844,785, 4,053,312, 4,055,428 and 4,076,529 (release after oxidation of carrier); U.S. Pat. No. 3,980,479, U.K. Patent Nos. 1,464,104 and 1,464,105 and U.S. Pat. No. 4,199,355 (release unless carrier is oxidized); and U.S. Pat. No. 4,139,379 (release after reduction of carrier).

The timing group of the DAR-compounds of the invention can be any organic linking group which will serve to join the development accelerator moiety to the carrier moiety and which, after its release from the carrier, will be cleaved from the development accelerator fragment. Such timing groups are described, e.g., in U.S. Pat. Nos. 4,248,962; 4,409,323; and 4,861,701.

When the DAR-compound is a developing agent of the type disclosed, for example, in U.S. Pat. No. 3,379,529, the development accelerator is imagewise released as a result of silver halide development by the developing agent, optionally in the presence of an auxiliary developing agent.

When the DAR-compound is a hydroquinone compound of the type described, for example, in European patent application 0,167,168, the development accelerator is imagewise released by a redox reaction in the presence of an oxidized developing agent.

When the DAR-compound is a coupler, the development accelerator group is imagewise released by a coupling reaction between the coupler and oxidized color developing agent. The carrier moiety can be any coupler moiety employed in conventional color photographic couplers which yield either colored or a colorless reaction product.

Especially preferred are coupler compounds, including both dye forming couplers and so called "universal" couplers which do not form a colored species on reaction with oxidized silver halide developing agent.

The development accelerator is typically blocked by attachment to the release compound via its silver halide binding site, e.g. the free valence sulfur atom of a mercapto inhibitor.

In order to obtain the full benefit of the released development accelerator, release moieties should be used which release the development acceleration early in the development step.

The release compounds are typically incorporated in silver halide color photographic elements in an amount that results in an increase in the rate at which silver halide in the element develops. This is evidenced by an increase in contrast ($\gamma$) of the processed element compared with an element from which the release compound is not present or is present in too great an amount. The amount will depend on the particular compound employed, but can be from an amount just effective to provide some evidence of development acceleration up to about 0.015 moles of accelerator group per mole silver halide.

Typically this amount would comprise from about 0.001 to about 0.015 moles accelerator group per mole silver halide.

Exemplary release compounds have the structures shown below in Table I.

In these structures, the symbols X, Y and Z represent the following groups

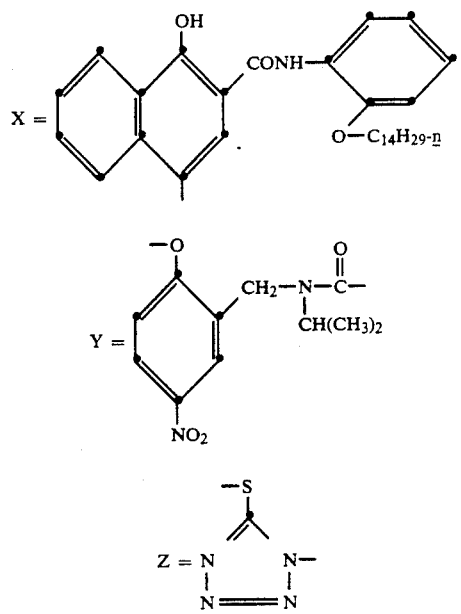

TABLE I

| Compound # | Structure |
|---|---|
| 1 | X<br>\|<br>Z—CH$_2$CH$_2$CH$_2$OCH$_3$ |
| 2 | X<br>\|<br>Y—Z—CH$_2$CH$_2$CH$_2$OCH$_3$ |
| 3 | X<br>\|<br>Z—CH$_2$—CH(OCH$_2$CH$_3$)$_2$ |
| 4 | X<br>\|<br>Y—Z—CH$_2$—CH(—O—CH$_2$—CH$_2$—CH$_2$—) (tetrahydrofuran ring) |
| 5 | X<br>\|<br>Z—CH$_2$—CH(—O—CH$_2$—CH$_2$—CH$_2$—) (tetrahydrofuran ring) |
| 6 | X<br>\|<br>Z—CH$_2$CH$_2$—C(=O)—OCH$_2$CH$_3$ |
| 7 | X<br>\|<br>Z—CH$_2$CH$_2$CH$_2$—C(=O)—OCH$_3$ |
| 8 | X<br>\|<br>Z—CH$_2$—CH$_2$—N(morpholino) |
| 9 | X<br>\|<br>Y—Z—CH$_2$—CH$_2$—N(morpholino) |
| 10 | X<br>\|<br>Z—CH$_2$CO$_2$CH$_2$CH$_3$ |

TABLE I-continued

| Compound # | Structure |
|---|---|
| 11 | 2,4-di-t-pentylphenoxy group with $C_2H_5$—CHCONH— linker to pyrazolone ring system bearing Z—$CH_2CO_2C_3H_7$ |
| 12 | $(CH_3)_3CCOCHCONH$— attached to chlorophenyl with $NHSO_2C_{16}H_{33}$, $CH_2NC_2H_5$, CO—Z—$CH_2CO_2C_3H_7$, and $NO_2$ substituents |
| 13 | X—O—(nitrophenyl)—$CH_2$—Z—$CH_2CO_2C_4H_9$ |

Release compounds of this invention can be prepared by methods known in the organic compound synthesis art. U.S. Pat. No. 4,782,012 describes illustrative syntheses in Synthesis Examples I–IV.

The release compounds of this invention can be incorporated in silver halide emulsions and the emulsions can be coated on a support to form a photographic element. Alternatively, the compound can be incorporated in the photographic element adjacent to the silver halide emulsion where, during development, it will be in reactive association with development products such as oxidized color developing agent.

The photographic elements in which the release compounds of this invention are employed can be either single color or multicolor elements. Multicolor elements contain dye image-forming units sensitive to each of the three primary regions of the spectrum. Each unit can be comprised of a single emulsion layer or of multiple emulsion layers sensitive to a given region of the spectrum. The layers of the element, including the layers of the image-forming units, can be arranged in various orders as known in the art.

A typical multicolor photographic element comprises a support bearing a cyan dye image-forming unit comprising at least one red-sensitive silver halide emulsion layer having associated therewith at least one cyan dye-forming coupler, a magenta image forming unit comprising at least one green-sensitive silver halide emulsion layer having associated therewith at least one magenta dye-forming coupler and a yellow dye image-forming unit comprising at least one blue-sensitive silver halide emulsion layer having associated therewith at least one yellow dye-forming coupler. The element can contain additional layers, such as filter layers, interlayers, overcoat layers, subbing layers, and the like. The layers of the element above the support typically have a total thickness of between about 5 and 30 microns.

In the following discussion of suitable materials for use in the elements of this invention, reference will be made to *Research Disclosure*, December 1989, Item 308119, published by Kenneth Mason Publications, Ltd., The Old Harbourmaster's, 8 North Street, Emsworth, Hampshire PO10 7DD, ENGLAND, the disclosures of which are incorporated herein by reference. This publication will be identified hereafter by the term "Research Disclosure."

The silver halide emulsions employed in the elements of this invention can be comprised of silver bromide, silver chloride, silver iodide, silver chlorobromide, silver chloroiodide, silver bromoiodide, silver chlorobromoiodide or mixtures thereof. The emulsions can include silver halide grains of any conventional shape or size. Specifically, the emulsions can include coarse, medium or fine silver halide grains. High aspect ratio tabular grain emulsions are specifically contemplated, such as those disclosed by Wilgus et al U.S. Pat. Nos. 4,434,226, Daubendiek et al 4,414,310, Wey 4,399,215, Solberg et al 4,433,048, Mignot 4,386,156, Evans et al 4,504,570, Maskasky 4,400,463, Wey et al 4,414,306, Maskasky 4,435,501 and 4,643,966 and Daubendiek et al 4,672,027 and 4,693,964. Also specifically contemplated are those silver bromoiodide grains with a higher molar proportion of iodide in the core of the grain than in the periphery of the grain, such as those described in GB 1,027,146; JA 54/48,521; U.S. Pat. Nos. 4,379,837; 4,444,877; 4,665,012; 4,686,178; 4,565,778; 4,728,602; 4,668,614; 4,636,461; EP 264,954. The silver halide emulsions can be either monodisperse or polydisperse as precipitated. The grain size distribution of the emulsions can be controlled by silver halide grain separation techniques or by blending silver halide emulsions of differing grain sizes.

Sensitizing compounds, such as compounds of copper, thallium, lead, bismuth, cadmium and Group VIII noble metals, can be present during precipitation of the silver halide emulsion.

The emulsions can be surface-sensitive emulsions, i.e., emulsions that form latent images primarily on the surfaces of the silver halide grains, or internal latent image-forming emulsions, i.e., emulsions that form latent images predominantly in the interior of the silver halide grains. The emulsions can be negative-working emulsions, such as surface-sensitive emulsions or unfogged internal latent image-forming emulsions, or direct-positive emulsions of the unfogged, internal latent image-forming type, which are positive-working when development is conducted with uniform light exposure or in the presence of a nucleating agent.

The silver halide emulsions can be surface sensitized. Noble metal (e.g., gold), middle chalcogen (e.g., sulfur, selenium, or tellurium), and reduction sensitizers, employed individually or in combination, are specifically contemplated. Typical chemical sensitizers are listed in Research Disclosure, Item 308119, cited above, Section III.

The silver halide emulsions can be spectrally sensitized with dyes from a variety of classes, including the polymethine dye class, which includes the cyanines, merocyanines, complex cyanines and merocyanines (i.e., tri-, tetra-, and poly-nuclear cyanines and merocyanines), oxonols, hemioxonols, styryls, merostyryls, and sterptocyanines. Illustrative spectral sensitizing dyes are disclosed in Research Disclosure, Item 308119, cited above, Section IV.

The release compounds are especially useful with silver iodohalide emulsions that are difficult to develop. Such emulsions include conventional and tabular grain emulsions having an equivalent circular diameter of 1.0 micron or more. The release compounds of 0.5 cubic microns or more. The release compounds are especially useful with silver halide emulsions that are free of sensitizing dye.

Suitable vehicles for the emulsion layers and other layers of elements of this invention are described in Research Disclosure Item 308119, Section IX and the publications cited therein.

In addition to the couplers described herein the elements of this invention can include additional couplers as described in Research Disclosure Section VII, paragraphs D, E, F and G and the publications cited therein. These additional couplers can be incorporated as described in Research Disclosure Section VII, paragraph C and the publications cited therein.

The coupler combinations of this invention can be used with bleach accelerator releasing couplers as described in European Patent Application 0,193,389 A and U.S. Pat. No. 4,912,024.

The coupler combinations of this invention can be used with colored masking couplers as described in U.S. Pat. No. 4,883,746.

The photographic elements of this invention can contain brighteners (Research Disclosure Section V), antifoggants and stabilizers (Research Disclosure Section VI), antistain agents and image dye stabilizers (Research Disclosure Section VII, paragraphs I and J), light absorbing and scattering materials (Research Disclosure Section VIII), hardeners (Research Disclosure Section XI), plasticizers and lubricants (Research Disclosure Section XII), antistatic agents (Research Disclosure Section XIII), matting agents (Research Disclosure Section XVI) and development modifiers (Research Disclosure Section XXI).

The photographic elements can be coated on a variety of supports as described in Research Disclosure Section XVII and the references described therein.

Photographic elements can be exposed to actinic radiation, typically in the visible region of the spectrum, to form a latent image as described in Research Disclosure Section XVIII and then processed to form a visible dye image as described in Research Disclosure Section XIX. Processing to form a visible dye image includes the step of contacting the element with a color developing agent to reduce developable silver halide and oxidize the color developing agent. Oxidized color developing agent in turn reacts with the coupler to yield a dye.

With negative working silver halide this processing step leads to a negative image. To obtain a positive (or reversal) image, this step can be preceded by development with a non-chromogenic developing agent to develop exposed silver halide, but not form dye, and then uniform fogging of the element to render unexposed silver halide developable. Alternatively, a direct positive emulsion can be employed to obtain a positive image.

Development is followed by the conventional steps of bleaching, fixing, or bleach-fixing, to remove silver and silver halide, washing and drying.

Typical bleach baths contain an oxidizing agent to convert elemental silver, formed during the development step, to silver halide. Suitable bleaching agents include ferricyanides, dichromates, ferric complexes of aminocarboxylic acids and persulfates.

Fixing baths contain a complexing agent that will solubilize the silver halide in the element and permit its removal from the element. Typical fixing agents include thiosulfates, bisulfites, and ethylenediamine tetraacetic acid.

In some cases the bleaching and fixing baths are combined in a bleach/fix bath.

The following examples illustrate synthesis of compounds of this invention.

SYNTHESIS EXAMPLE I

Preparation of intermediate
S-2,1-(3-methoxypropyl)-2-tetrazoline-5-thione

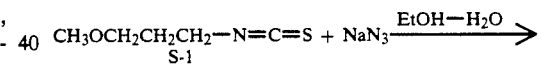

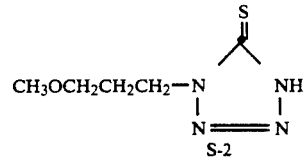

To a mechanically stirred slurry of 50 g (0.382 mole) of 3-methoxypropylisothiocyanate (S-1) in 200 ml ethanol under a nitrogen atmosphere was added in a slow stream 49.6 g (0.694 mole) of sodium azide dissolved in 300 ml water. The resultant solution was refluxed for 16 hrs, cooled to room temperature (20° C.) and filtered. The filtrate was extracted twice with ether, and then acidified to pH=1 with concentrated hydrochloric acid. The resultant solution was extracted with methylene chloride, and the methylene chloride extract washed with saturated brine (NaCl solution), dried over magnesium sulfate and evaporated to yield intermediate S-2 as an oil.

SYNTHESIS II

Preparation of Carbamoyl Chloride Intermediate S-4

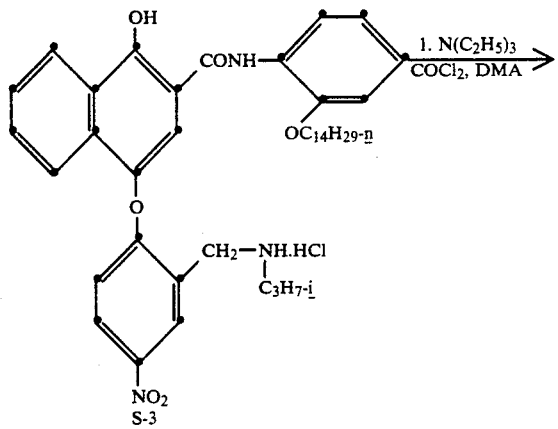

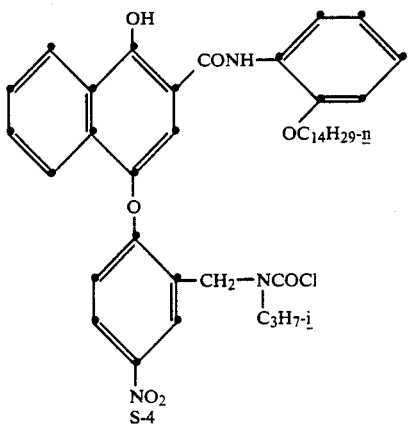

A slurry of S-3 amine hydrochloride (38.8 g, 0.054 mole) and triethylamine (5.45 g, 0.054 mole) in 300 ml dry tetrahydrofuran was stirred at room temperature (20° C.) under a nitrogen atmosphere for one hour and then filtered, N,N-dimethylaniline (9.1 g, 0.075 mole) was added to the filtrate and the resulting mixture added dropwise to 100 ml of the stirred 12% phosgene in toluene solution. The reaction was cooled in an ice-acetone bath under a nitrogen atmosphere.

After one hour, the reaction mixture was filtered and the filtrate concentrated in vacuo and the resulting gum (S-4) used directly in the next reaction.

SYNTHESIS EXAMPLE VII

Preparation of Compound 2

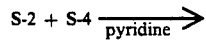

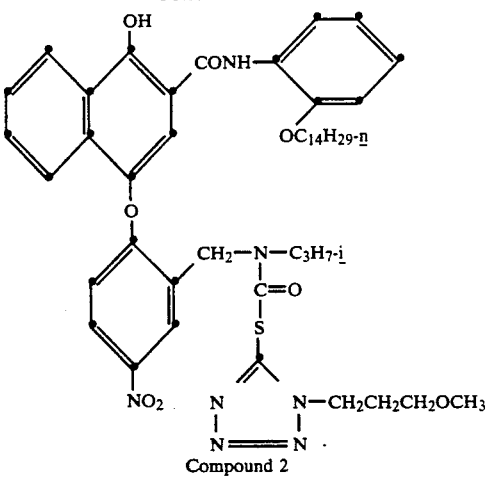

Compound 2

To a room temperature solution of carbamoyl chloride (S-2) (0.03 mole from the previous reaction) in 250 ml pyridine was added in one portion 5 g (0.029 mole) of intermediate S-4, 1-(3-methoxypropyl)-2-tetrazoline-5-thione, and the resultant solution stirred for sixteen hours under a nitrogen atmosphere. The reaction mixture was then quenched in ca. 1.5 l ice-water mixture containing 150 ml concentrated hydrochloric acid. The mixture was extracted with ethyl acetate. The extract was then washed sequentially with 5% hydrochloric acid, 5% sodium carbonate, brine, dried over anhydrous magnesium sulfate, filtered and evaporated in vacuo. The resultant oil was crystallized from hexane-ethyl acetate to yield an off-white solid, m.p. 92°–7° C.

The elemental analysis was correct for Compound 2. Calculated: C, 63.9; H, 7.0; N, 11.1; S, 3.6; Found: C, 64.1; H, 7.0; N, 11.1; S, 3.7.

SYNTHESIS EXAMPLE III

Preparation of intermediate S-6, 1-(2-tetrahydrofurfuryl)-2-tetrazoline-5-thione

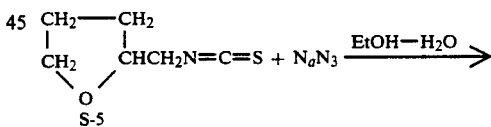

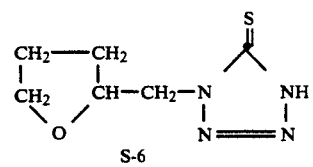

To a mechanically stirred slurry of 50 g (0.382 mole) of (2-tetrahydrofurfuryl) isothiocyanate (S-5) in 200 ml ethanol under a nitrogen atmosphere was added in a slow stream 35 g (0.489 mole) of sodium azide dissolved in 300 ml water. The resultant solution was refluxed for 16 hrs, cooled to room temperature (20° C.) and filtered. The filtrate was extracted twice with ether, and then acidified to pH=1 with concentrated hydrochloric acid. The resultant solution was extracted with methylene chloride, and the methylene chloride extract washed with saturated brine (NaCl solution), dried over magnesium sulfate and evaporated to yield intermediate S-6 as an oil.

SYNTHESIS EXAMPLE IV

Preparation of Compound 4

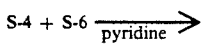

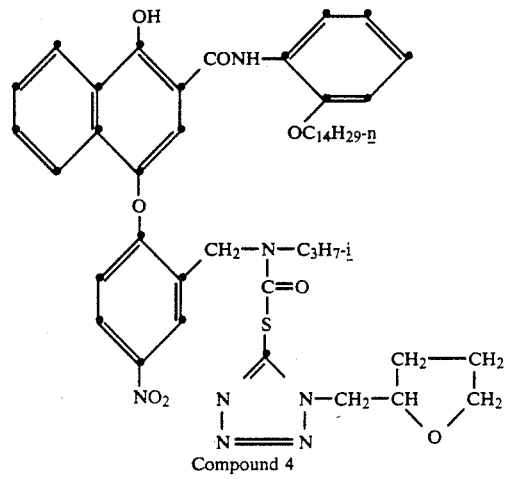

Compound 4

To a room temperature solution of 25 g carbamoyl chloride (S-4) (0.033 mole) 200 ml pyridine was added in one portion 5.5 g (0.030 mole) of intermediate S-6 1-(2-tetrahydrofurfuryl)-2-tetrazoline-5-thione, and the resultant solution stirred for sixteen hours under a nitrogen atmosphere.

The reaction mixture was then quenched in ca. 1.5 l ice-water mixture containing 150 ml concentrated hydrochloric acid. The mixture was extracted with ethyl acetate. The extract was then washed sequentially with 5% hydrochloric acid, 5% sodium carbonate, brine, dried over anhydrous magnesium sulfate, filtered and evaporated in vacuo. The resultant oil was crystallized from hexane-ethyl acetate to yield 1.4 g of an off-white solid, m.p. 65°-8° C.

The elemental analysis was correct for Compound 4. Calculated: C, 64.4; H, 6.3; N, 11.0; S, 3.6; Found: C, 64.9; H, 6.8; N, 10.8; S, 4.0.

SYNTHESIS EXAMPLE V

Preparation of intermediate S-8, 1-(2-morpholinoethyl)-2-tetrazoline-5-thione

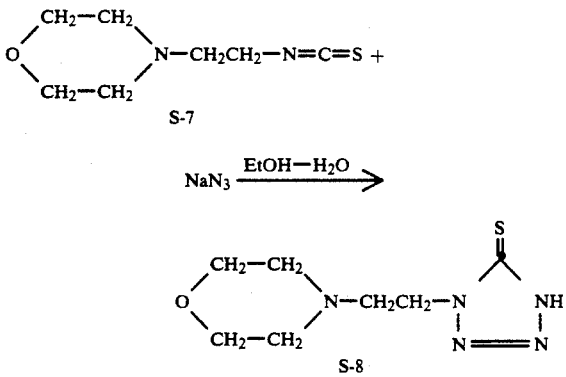

To a mechanically stirred slurry of 25.8 g (0.15 mole) of 2-morpholinoethylisothiocyanate (S-7) in 250 ml ethanol under a nitrogen atmosphere was added in a slow stream 19.5 g (0.3 mole) of sodium azide dissolved in 600 ml water. The resultant solution was refluxed for 16 hrs, cooled to room temperature (20° C.) and filtered. The filtrate was extracted twice with ether, and then acidified to pH=1 with concentrated hydrochloric acid. The resultant solution was extracted three times with ether. The pH of the aqueous solution was adjusted to 4.5 using a 50% NaOH solution and a fine white precipitate formed. The precipitate was collected by filtration to yield 17.1 grams of intermediate S-8 with a melting point of 226°-8° C.

SYNTHESIS EXAMPLE VI

Preparation of Compound 8

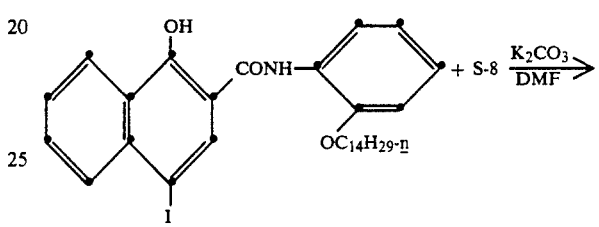

S-9

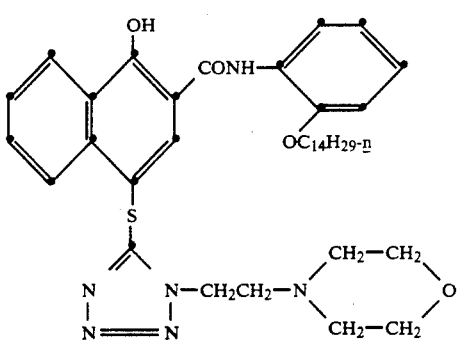

Compound 8

A slurry of 3.6 g (0.026 mole) of $K_2CO_3$ in 200 ml dimethylformamide (DMF) was added to a flask containing a 23.5 g (0.039 mole) of coupler S-9 and 5.6 g (0.026 mole) of intermediate S-8, 1-(2-morpholinoethyl)-2-tetrazoline-5-thione. This mixture was then heated on a steam bath, under a nitrogen atmosphere. After 3 hours, the mixture was added to 500 ml of ice water, and the resultant mixture extracted with ethyl acetate. The ethyl acetate extract was washed sequentially with a 5% sodium carbonate solution, a 5% hydrochloric acid solution and a saturated brine solution, and then dried over anhydrous magnesium sulfate. The organic solution was chromatographed over silica gel using an ethyl acetate/methylene chloride eluant, and evaporated to produce a solid. The solid was recrystallized from methanol to yield 6.2 g of compound 8, showing melting point of 107°-8° C.

The elemental analysis was correct for Compound 8. Calculated: C, 66.2; H, 7.6; N, 12.2; S, 4.7; Found: C, 66.2; H, 7.8; N, 12.1; S, 4.5.

EXAMPLE I

Comparison of Development Inhibiting and Development Accelerating Effect as a Function of Compound Level and Structure A series of 26 photographic elements were prepared having the following structure and composition. Unless otherwise indicated the numbers following a component represents the amount of the component in the element, expressed in $g/m^2$.

Element 1 was prepared by sequentially applying the following layers to a clear support:

Antihalation layer (layer 1): gelatin at 2.45 g, grey colloidal silver at 0.33 g, 2,5-didodecylhydroquinone at 0.12 g.

Photographic layer (layer 2): gelatin at 2.4 g, red sensitized silver iodobromide emulsion (6.4 mol % I, 0.53 microns equivalent circular diameter) at 1.6 g silver, yellow dye-forming coupler Ya at 1.3 g.

Interlayer (layer 3): gelatin at 0.62 g and 2,5-didodecylhydroquinone at 0.12 g.

Photographic layer (layer 4): gelatin at 2.4 g, green sensitized silver iodobromide emulsion (6.4 mol % I, 0.53 microns equivalent circular diameter) at 1.6 g silver, cyan dye-forming coupler Ca at 0.75 g. Inventive and control compounds were added to this layer as indicated in Table 2.

Protective Overcoat (layer 5): gelatin at 2.5 g and bisvinylsulfonylmethane as gelatin hardener at 1.75% by weight to total gelatin.

Elements 2 through 26 were prepared in a manner analogous to Element 1, the control sample which contains no release compound, by adding the comparison or DAR compound to photographic layer 4 at the level indicated in Table 2.

The dye-forming couplers for the photographic layers were each dispersed in half their weight of di-n-butyl phthalate, while the DAR compounds were each dispersed in twice their weight of diethyl lauramide.

Cyan dye-forming coupler Ca:

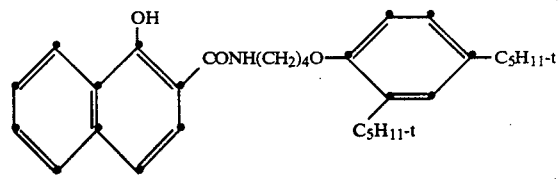

Yellow dye-forming coupler Ya:

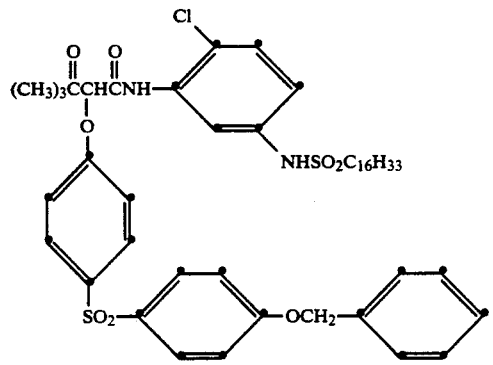

The elements were exposed through a graduated-density test object and Kodak Wratten 99 (green) filter. This exposed photographic layer 4.

The materials were then processed at 38° C. as follows:

| Color Developer | 2.75' |
|---|---|
| Stop (5% Acetic Acid) | 2' |
| Wash | 2' |
| Bleach-Fe(CN)$_6$ | 2' |
| Fix | 2' |
| Wash | 2' |

The color developer composition was:

| $K_2SO_3$ | 2.0 g/l |
|---|---|
| 4-amino-3-methyl-N-ethyl-N-beta-hydroxyethylaniline sulfate | 3.35 g/l |
| $K_2CO_3$ | 30.0 g/l |
| KBr | 1.25 g/l |
| KI | 0.0006 g/l |
| adjusted to pH = 10.0 | |

The oxidized color developing agent generated by development of exposed silver reacts with adjacent image dye-forming compounds and DAR compounds to form dyes and to release accelerator in photographic layer 4. The development accelerating effects of the accelerator released from the DAR compound can be assessed by monitoring the gamma of photographic layer 4.

In addition to the control element, which contained no release compound, individual elements contained a release compound of the invention identified in Table 1, above, in an amount shown in Table 2, below, or one of the following comparison known development inhibitor release compounds.

Comparison DIR Compounds

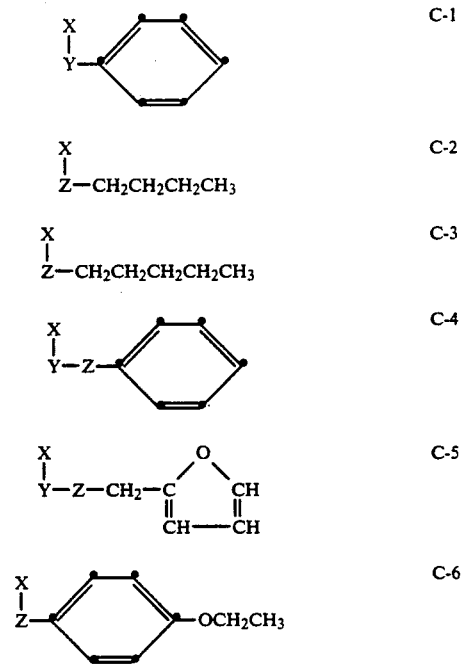

TABLE 2

Comparison of Development Inhibiting an Development Accelerating Effect as a Function of Compound Level and Structure.

| Element | Compound | Quantity[a] (g/m²) | mole ratio | Accelerator[b] Groups | Relative[c] Gamma |
|---|---|---|---|---|---|
| 1 | none | 0 | 0 | 0 | 100 |
| 2 | C-1 | 0.036 | 0.0036 | 0 | 39 |
| 3 | C-2 | 0.036 | 0.0036 | 0 | 50 |
| 4 | C-3 | 0.036 | 0.0036 | 0 | 37 |
| 5 | 1 | 0.037 | 0.0037 | 1 | 135 |
| 6 | 2 | 0.050 | 0.0037 | 1 | 132 |
| 7 | 2 | 0.068 | 0.0052 | 1 | 138 |
| 8 | C-4 | 0.068 | 0.0052 | 0 | 38 |
| 9 | C-5 | 0.069 | 0.0051 | 1 | 68 |
| 10 | 4 | 0.069 | 0.0051 | 1 | 121 |
| 11 | 4 | 0.206 | 0.0151 | 1 | 88 |
| 12 | 5 | 0.036 | 0.0036 | 1 | 123 |
| 13 | 5 | 0.177 | 0.0177 | 1 | 96 |
| 14 | 8 | 0.036 | 0.0035 | 2 | 132 |
| 15 | 8 | 0.109 | 0.0105 | 2 | 132 |
| 16 | 9 | 0.071 | 0.0051 | 2 | 118 |
| 17 | 9 | 0.142 | 0.0105 | 2 | 115 |
| 18 | 9 | 0.213 | 0.0153 | 2 | 112 |
| 19 | 6 | 0.036 | 0.0036 | 1 | 129 |
| 20 | 6 | 0.178 | 0.0178 | 1 | 97 |
| 21 | 7 | 0.037 | 0.0036 | 1 | 110 |
| 22 | 7 | 0.109 | 0.0108 | 1 | 96 |
| 23 | 7 | 0.213 | 0.0178 | 1 | 77 |
| 24 | 10 | 0.036 | 0.0036 | 1 | 117 |
| 25 | 10 | 0.178 | 0.0181 | 1 | 92 |
| 26 | C-6 | 0.038 | 0.0036 | 1 | 36 |

Footnotes:
[a]The quantity of compound added to Photographic Layer 4 expressed in g/m² and expressed as the moles of added compound per mole of silver incorporated in Photographic Layer 4.
[b]The total number of ether oxygen and imino-nitrogen atoms in the Q group of the compound added to Photographic Layer 4.
[c]The relative gamma is:
$$\frac{\text{Gamma (Layer 4 of invention or comparison element)}}{\text{Control Gamma (Layer 4 of element 1)}} \times 100$$

A relative gamma greater than 100 indicates that development acceleration has occurred while a relative gamma less than 100 indicates that development inhibition has occurred.

This data shows that incorporation of an ether oxygen or imino-nitrogen group in a ballast (the Q group) surprisingly turns a DIR compound into a DAR compound when the compound is used in small amounts. Specific comparisons illustrating this effect are element 5 (CCCOC ballast) vs elements 3 (CCCC ballast) and 4 (CCCCC ballast).

Further, this data shows that the development acceleration function occurs in the presence or absence of timing groups. Specific comparisons illustrating this effect are element 5 vs element 6; element 10 vs element 12; and element 14 vs element 16.

Additionally, this data shows that the incorporation of other silver halide bonding sites into the compounds reduces the development acceleration function and turns the materials back into development inhibitors. Specific examples of this effect are illustrated by comparison of element 10 and element 9. Element 2 and element 26 further illustrate this point.

In addition, this data shows that incorporation of more than one ether oxygen and/or imino-nitrogen groups into a ballast enhances the development accelerating function and enables the function to be realized at higher coated levels. This is illustrated by comparison of inventive elements 14 through 18 to comparison elements 20, 22, 23 and 24 inter alia.

Inventive elements 19, 21 and 24 additionally illustrate that the ether oxygen group can be adjacent to an carbonyl group without any loss in function.

EXAMPLE II

Comparison of Development Inhibiting and Development Accelerating Effect in an Adjacent Layer as a Function of Compound Level and Structure Photographic Elements 1 through 26 prepared as described above were exposed through a graduated density test object and a KODAK Wratten 12 filter (minus blue). This procedure gives equal effective exposure to both photographic layer 2 and photographic layer 4.

These elements were then processed as in Photographic Example I. Under these conditions, both photographic layer 2 and photographic layer 4 develop. During development, the DAR compound incorporated in layer 4 liberates the development accelerator moiety in photographic layer 4. The moiety is mobile and enables acceleration in both photographic layer 4 and in photographic layer 2. The accelerating effects of the DAR compounds released as a function of development in photographic layer 4 on development in photographic layer 2 can then be assessed by monitoring the gamma of photographic layer 2. An increase in the gamma over that encountered for photographic layer 2 in photographic element 1 indicates an accelerating effect while a decrease in the gamma below that encountered for photographic layer 2 in photographic element 1 indicates an inhibiting effect. The larger the decrease in gamma, the larger the inhibiting interimage effect of photographic layer 4 onto photographic layer 2.

TABLE 3

Comparison of Development Inhibiting an Development Accelerating Effect in an Adjacent Layer as a Function of Compound Level and Structure.

| Element | Compound | Quantity[a] (g/m²) | mole ratio | Accelerator[b] Groups | Relative[c] Gamma |
|---|---|---|---|---|---|
| 1 | none | 0 | 0 | 0 | 100 |
| 2 | C-1 | 0.036 | 0.0036 | 0 | 63 |
| 3 | C-2 | 0.036 | 0.0036 | 0 | 86 |
| 4 | C-3 | 0.036 | 0.0036 | 0 | 78 |
| 5 | 1 | 0.037 | 0.0037 | 1 | 134 |
| 6 | 2 | 0.050 | 0.0037 | 1 | 133 |
| 7 | 2 | 0.068 | 0.0052 | 1 | 140 |
| 8 | C-4 | 0.068 | 0.0052 | 0 | 36 |
| 9 | C-5 | 0.069 | 0.0051 | 1 | 60 |
| 10 | 4 | 0.069 | 0.0051 | 1 | 109 |
| 11 | 4 | 0.206 | 0.0151 | 1 | 58 |
| 12 | 5 | 0.036 | 0.0036 | 1 | 125 |
| 13 | 5 | 0.177 | 0.0177 | 1 | 71 |
| 14 | 8 | 0.036 | 0.0035 | 2 | 116 |
| 15 | 8 | 0.109 | 0.0105 | 2 | 93 |
| 16 | 9 | 0.071 | 0.0051 | 2 | 122 |
| 17 | 9 | 0.142 | 0.0105 | 2 | 108 |
| 18 | 9 | 0.213 | 0.0153 | 2 | 103 |
| 19 | 6 | 0.036 | 0.0036 | 1 | 131 |
| 20 | 6 | 0.178 | 0.0178 | 1 | 73 |
| 21 | 7 | 0.037 | 0.0036 | 1 | 125 |
| 22 | 7 | 0.109 | 0.0108 | 1 | 86 |
| 23 | 7 | 0.213 | 0.0178 | 1 | 66 |
| 24 | 10 | 0.036 | 0.0036 | 1 | 112 |
| 25 | 10 | 0.178 | 0.0181 | 1 | 65 |

TABLE 3-continued

Comparison of Development Inhibiting an Development Accelerating Effect in an Adjacent Layer as a Function of Compound Level and Structure.

| Element | Compound | Quantity[a] (g/m²) | mole ratio | Accelerator[b] Groups | Relative[c] Gamma |
|---|---|---|---|---|---|
| 26 | C-6 | 0.038 | 0.0036 | 1 | 81 |

Footnotes:
[a] The quantity of compound added to Photographic Layer 4 expressed in g/m² and expressed as the moles of added compound per mole of silver incorporated in Photographic Layer 4.
[b] The total number of ether oxygen and imino-nitrogen atoms in the Q group of the compound added to Photographic Layer 4.
[c] The relative gamma is:

$$\frac{\text{Gamma (Layer 2 of invention or comparison element)}}{\text{Control Gamma (Layer 2 of element 1)}} \times 100$$

The relative gamma data provided in Table 3 illustrates that the inventive elements enable development acceleration in photographic layers other than the one in which they are incorporated.

The invention has been described in detail with particular reference to preferred embodiments thereof, but it will be understood that variations and modifications can be effected within the spirit and scope of the invention.

What is claimed is:

1. A photographic element having a support, a silver halide emulsion layer and, associated with that layer, a development accelerator releasing compound that releases a development accelerator having the structure

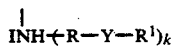

where INH is a silver halide binding group having sulfur, selenium, tellurium, heterocyclic nitrogen or heterocyclic carbon with a free valence that can form a bond to a silver atom, Q is an aliphatic or alicyclic group of 2 to 30 carbon atoms which comprises an ether oxygen and/or imino nitrogen and is free of silver halide bonding sites, and k is 1–4;

the compound being present in the element in an amount such that when processed, the element provides an increase in contrast ($\gamma$) compared to an element identically formulated and processed except that it does not contain the development accelerator releasing compound.

2. A photographic element of claim 1, wherein the development accelerator has the structure:

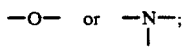

where
R is an optionally substituted alkylene or cycloalkylene of 2–10 carbon atoms;
Y is —O— or 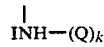

$R^1$ is an optionally substituted alkyl or cycloalkyl of 1 to 6 carbon atoms when Y is —O—, or $R^1$ is an optionally substituted alkylene or cycloalkylene of 1 to 6 carbon atoms when Y is

the unsatisfied bond of N being joined to $R^1$; and
R and $R^1$ may be joined to form a cyclic structure.

3. A photographic element of claim 1 wherein the development accelerator releasing compound is present in a layer containing silver halide grains that are free of spectral sensitizing dye and have an equivalent circular diameter of greater than 1.0 micron.

4. A photographic element of claim 1 wherein the INH is a mercaptotetrazole.

5. A photographic element of claim 1 wherein the development accelerator is released from the compound as a result of a coupling reaction between the compound and oxidized silver halide developing agent.

6. A photographic element of claim 5, wherein the development accelerator releasing compound is a yellow or cyan dye forming coupler.

7. A photographic element having a support, a silver halide emulsion layer and, associated with that layer, a development accelerator releasing compound that releases a development accelerator having the structure

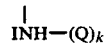

where INH is a tetrazole, a mercaptotetrazole or a benzotriazole silver halide binding group having sulfur, selenium, tellurium, heterocyclic nitrogen or heterocyclic carbon with a free valence that can form a bond to a silver atom, Q is an aliphatic or alicyclic group of 2 to 30 carbon atoms which comprises an ether oxygen and/or imino nitrogen and is free of silver halide bonding sites, and k is 1–4;

the compound being present in the element in an amount such that when processed, the element provides an increase in contrast ($\gamma$) compared to an element identically formulated and processed except that it does not contain the development accelerator releasing compound.

8. A photographic element of claim 1 or 11 wherein the development accelerator releasing compound is present in the element in an amount of from 0.001 to 0.015 moles acceleration group per mole silver halide in the layer with which it is associated.

9. A photographic element having a support, a silver halide emulsion layer and, associated with that layer, a development accelerator releasing compound that releases a development accelerator having one of the structures:

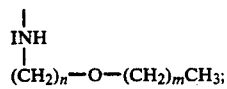

-continued

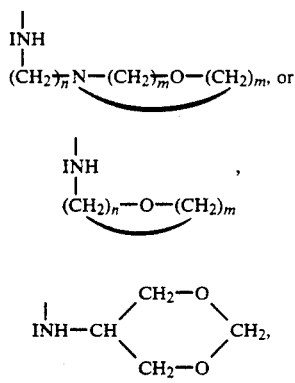

-continued $$INH \!\!-\!\!(CH_2)_{\overline{n}} O \!\!-\!\!(CH_2)_{\overline{m}} OCH_3$$

where INH is a silver halide binding group having sulfur, selenium, tellurium, heterocyclic nitrogen or heterocyclic carbon with a free valence that can form a bond to a silver atom;

each n is independently an integer of 2 to 5; and m is an integer of 2 to 6;

the compound being present in the element in an amount such that when processed, the element provides an increase in contrast ($\gamma$) compared to an element identically formulated and processed except that it does not contain the development accelerator releasing compound.

* * * * *